(12) United States Patent
Zhang et al.

(10) Patent No.: US 11,096,251 B2
(45) Date of Patent: Aug. 17, 2021

(54) CALCULATION METHOD FOR OPERATING RESISTANCE IN DUAL-ELECTRODE DC ELECTRIC-SMELTING FURNACE FOR MAGNESIUM

(71) Applicant: Northeastern University, Shenyang (CN)

(72) Inventors: Yingwei Zhang, Shenyang (CN); Xiaoguang Xue, Shenyang (CN); Yongxu Li, Shenyang (CN)

(73) Assignee: NORTHEASTERN UNIVERSITY, Shenyang (CN)

( * ) Notice: Subject to any disclaimer, the term of this patent is extended or adjusted under 35 U.S.C. 154(b) by 62 days.

(21) Appl. No.: 16/093,849

(22) PCT Filed: May 21, 2018

(86) PCT No.: PCT/CN2018/087694
§ 371 (c)(1),
(2) Date: Oct. 15, 2019

(87) PCT Pub. No.: WO2019/091084
PCT Pub. Date: May 16, 2019

(65) Prior Publication Data
US 2020/0084845 A1    Mar. 12, 2020

(30) Foreign Application Priority Data
Nov. 8, 2017 (CN) .......................... 201711092050.7

(51) Int. Cl.
*H05B 7/20* (2006.01)
*G01R 27/08* (2006.01)
*G06F 17/13* (2006.01)

(52) U.S. Cl.
CPC ............... *H05B 7/20* (2013.01); *G01R 27/08* (2013.01); *G06F 17/13* (2013.01)

(58) Field of Classification Search
CPC ... H05B 7/20; H05B 7/18; H05B 7/00; G01R 27/08; G01R 27/02; G01R 27/00;
(Continued)

(56) References Cited

U.S. PATENT DOCUMENTS

| 4,029,888 A | * | 6/1977 | Roberts | ................... | H05B 7/152 |
| | | | | | 373/105 |
| 4,663,764 A | * | 5/1987 | Bretthauer | ............. | H05B 7/148 |
| | | | | | 373/104 |

(Continued)

FOREIGN PATENT DOCUMENTS

| CN | 107045284 A | 8/2017 |
| CN | 103102061 A | 5/2018 |

(Continued)

OTHER PUBLICATIONS

Chih Wei Wu, "Data-Driven Abnormal Condition Identification and Self-healing Control Method for Fused Magnesium Furnace", China Doctoral Thesis, Mar. 31, 2017, pp. 1-27, vol. 2017/03, Chapter 4, ISSN: 1674-022.

*Primary Examiner* — Mohamed Charioui
(74) *Attorney, Agent, or Firm* — Muncy, Geissler, Olds & Lowe, P.C.

(57) ABSTRACT

The invention provides a calculation method for operating resistance in a dual-electrode DC electric-smelting furnace for magnesium, including the following steps of: calculating a raw material resistance: simplifying a raw material model as an electrode-centered cylindrical model, determining an electric-field strength of each point in an electric field generated by a raw material layer around an electrode in the cylindrical model, calculating a raw material voltage between two electrodes according to the electric-field strength of each point in the electric field, and further obtaining the raw material resistance between the two electrodes; calculating an electric arc-resistance relation model:

(Continued)

determining a relation between an actual electric arc length and a distance from the electrode to a surface of a smelting pool, and calculating a relation between an electric arc voltage and the actual electric arc length, namely the electric arc-resistance relation model; and calculating a smelting pool resistance, namely the sum in series of the smelting pool resistance of the two electrodes.

6 Claims, 7 Drawing Sheets

(58) Field of Classification Search
CPC .......... G06F 17/13; G06F 17/11; G06F 17/10; G06F 17/00; G16C 20/10; G16C 20/00
See application file for complete search history.

(56) References Cited

U.S. PATENT DOCUMENTS 5,115,447 A * 5/1992 Bowman ................. F27D 19/00
373/102
2009/0054242 A1 2/2009 Takahashi et al.

FOREIGN PATENT DOCUMENTS

CN 108021783 A 5/2018
WO WO-2006089315 A1 * 8/2006 ............. H05B 7/148

* cited by examiner

CALCULATION METHOD FOR OPERATING RESISTANCE IN DUAL-ELECTRODE DC ELECTRIC-SMELTING FURNACE FOR MAGNESIUM

BACKGROUND OF THE INVENTION

1. Field of the Invention

The invention belongs to the technical field of industrial magnesite electric-smelting, and particularly relates to a calculation method for operating resistance in a dual-electrode DC electric-smelting furnace for magnesium.

2. The Prior Arts

Currently, an industrial electric-smelting furnace for magnesium is mainly used for production of electrically-smelted magnesium, the production process comprises the following steps of firstly, smashing solid electrically smelted magnesium into powder; then, adding the powder to the electric-smelting furnace for magnesium, and inserting electrodes (after power is powered on, the electrically-smelted magnesium is smelted mainly by heat from electrode arcs); lifting the electrodes out of the furnace after smelting is completed; and moving cooled electrically-smelted magnesium out of the electric-smelting furnace for magnesium for natural crystallization. The composition and operating principles of dual-electrode electric-smelting furnace for magnesium are as shown in FIG. 1, wherein 1 indicates transformer, 2 indicates short net, 3 indicates thyristor circuit, 4 indicates graphite electrode, 5 indicates furnace shell, 6 indicates cart body, 7 indicates electrode holder, 8 indicates raw material, 9 indicates electric arc, and 10 indicates smelting pool.

In a dual-electrode DC electrical model for electrically-smelted magnesium, numerous kinds of resistance, including transformer resistance, thyristor resistance, short net resistance, raw material resistance, smelting pool resistance and electric arc resistance exist. The above resistance has a significant effect on the smelting process of magnesium oxide, and some of the resistance plays a critical part in the design of the electric-smelting furnace for magnesium. The fluctuation in transformer resistance, short net resistance and the thyristor will have a great adverse impact on constant-current regulation. Therefore, it is the most important to ensure the stability of the above resistance. Furthermore, electric arcs are a critical factor of smelting operation as well as a direct energy supplier for magnesium oxide smelting. The length of an electric arc has a certain relation with the voltage of the electric arc, the electric arc can cause an arc deflection effect under the influence of a magnetic field, which can also affect the voltage of the electric arc. The arc deflection effect should also be considered during setting the distance between electrodes. Raw material resistance and smelting pool resistance are collectively called operating resistance in practical application. The raw material resistance can consume some of the energy of the electrical model, and resistance heat generated therefrom plays a significant role in the uniform smelting of raw materials. A constant current mode and a constant resistance mode are commonly used in automatic electrode regulation, wherein constant-current regulation ensures in essence the stability of the electric arc length by ensuring the stability of the current, thereby guaranteeing continuation of the smelting process. As resistance has a close relationship with power, through resistance regulation, the power model can be well controlled and further the process is controlled. Therefore, it is greatly important to study the operating resistance in the electric-smelting furnace for magnesium.

Compared with a three-phase AC electric-smelting furnace for magnesium, the dual-electrode DC electric-smelting furnace for magnesium differs mainly in the fact that AC power supply on the secondary side of the transformer is converted into DC power supply, two graphite electrodes are used to replace three graphite electrodes, and the AC electric arc is replaced by the DC electric arc. FIG. 3 shows a circuit diagram of the dual-electrode electric-smelting furnace for magnesium. For facilitating the analysis of operating resistance, FIG. 2 shows a model diagram of the positions of graphite electrodes in the smelting process.

SUMMARY OF THE INVENTION

In view of problems existing in the prior art, the invention provides a calculation method for operating resistance in the dual-electrode DC electric-smelting furnace for magnesium.

The technical solution lies in that the calculation method for operating resistance in the dual-electrode DC electric-smelting furnace for magnesium comprises the following steps of: calculating a raw material resistance: simplifying a raw material model as an electrode-centered cylindrical model, determining an electric-field strength of each point in an electric field generated by a raw material layer around an electrode in the cylindrical model, calculating a raw material voltage between two electrodes according to the electric-field strength of each point in the electric field, and further obtaining the raw material resistance between the two electrodes; calculating an electric arc-resistance relation model: determining a relation between an actual electric arc length and a distance from the electrode to a surface of a smelting pool, and calculating a relation between an electric arc voltage and the actual electric arc length, namely the electric arc-resistance relation model; and calculating a smelting pool resistance, namely a sum in series of the smelting pool resistance of the two electrodes.

The calculating raw material resistance comprises: simplifying the raw material model as the electrode-centered cylindrical model according to an inserting depth of the electrode in a raw material and a distance between center lines of the two electrodes in the dual-electrode DC electric-smelting furnace for magnesium; determining the electric-field strength of each point in the electric field generated by the raw material layer around the electrode in the cylindrical model; and integrating the electric-field strength being x away from the center line of the electrode in the cylindrical model from a surface of the electrode to half the distance between the center lines of the two electrodes to obtain half the raw material voltage between the two electrodes, and calculating the raw material voltage between the two electrodes so as to further obtain the raw material resistance.

The calculating electric arc-resistance relation model comprises: determining the model of the electric arc-resistance relation; describing the electric arc voltage according to changes of an ideal electric arc length and a current; establishing an electric arc magnetic-field model and an electric arc deflection trajectory model by assumptions on shape and position of electric arcs during an operation of the electric-smelting furnace for magnesium; determining a relation between the actual electric arc length and the ideal electric arc length in combination with a radius of the electric arc deflection trajectory as well as the electric arc deflection trajectory model; and calculating the relation between the electric arc voltage and the actual electric arc length, namely the electric arc-resistance relation model.

The electric arc deflection trajectory model is as follows:

$$L_a = R_a \arcsin\left(\frac{L}{R_a}\right)$$

wherein $R_a$ is an electric arc deflection trajectory radius, $L_a$ is the actual electric arc length and L is the ideal electric arc length namely the distance from the electrode to a surface of the smelting pool.

The step for establishing the electric arc magnetic-field model and the electric arc deflection trajectory model by assumptions on the shape and position of the electric arcs during the operation of the electric-smelting furnace for magnesium specially comprises: making theoretical model assumptions on actual electric arcs, and establishing the electric arc magnetic-field model, namely a sum of an electrode-generated magnetic field and an electric arc-generated magnetic field; and determining a motion trajectory of the electric arcs in an X-Y plane, namely, the electric arc deflection trajectory following a circular path, and establishing the electric arc deflection trajectory model.

The step for performing theoretical model assumptions on the actual electric arc specially comprises that: the electric arcs are assumed to have mutual deflections only, namely a main electric arc deflection effect occurs in a plane defined by the two electrodes; an electrode length is assumed to be infinite, namely an ultimate effect is ignored; the electric arcs are assumed to follow a straight line in deflection; and an effect of the magnetic field generated by the current of the smelting pool on the electric arc is ignored.

The calculating smelting pool resistance comprises: simplifying a smelting pool model as a semi-sphere model with a bottom center of the electrode as a center of a sphere and a distance from a bottom of the electrode to a surface of the smelting pool as a radius; calculating an electric-field strength of a spherical surface being r away from the center of the sphere in the semi-sphere model; integrating the electric-field strength being r away from the center of sphere in the semi-sphere model from the bottom of the electrode to the surface of the smelting pool so as to obtain a voltage drop from the bottom of the single electrode to the surface of the smelting pool; and calculating the sum in series of the smelting pool resistance of the two electrodes, namely the determined smelting pool resistance.

The calculation method has the beneficial effects that the length of an electric arc has a certain relation with the voltage of the electric arc, the electric arc can cause an arc deflection effect under the influence of a magnetic field, which can also affect the voltage of the electric arc. Therefore, the arc deflection effect should also be considered during setting the distance between electrodes. The raw material resistance and smelting pool resistance are collectively called operating resistance in practical application. The raw material resistance can consume some of the energy of the electrical model, and resistance heat generated therefrom plays a significant role in the uniform smelting of raw materials. As resistance has a close relationship with power, through resistance regulation, power output can be well controlled, and the operation process of the electric-smelting furnace for magnesium can be further controlled.

DETAILED DESCRIPTION OF THE PREFERRED EMBODIMENT

The embodiment of the invention will be detailed below in combination with the drawings.

A calculation method for operating resistance in the dual-electrode DC electric-smelting furnace for magnesium comprises the following steps of:

Step 1: calculating raw material resistance: simplifying the raw material model as an electrode-centered cylindrical model, determining the electric-field strength of each point in the electric field generated by the raw material layer around the electrode in the cylindrical model, calculating the raw material voltage between the two electrodes according to the electric-field strength of each point in the electric field, and further obtaining the raw material resistance between the two electrodes.

Step 1.1: simplifying the raw material model as an electrode-centered cylindrical model according to the inserting depth $h_l$ of the electrode in the raw material and the distance $\delta_e$ between the center lines of the two electrodes in the dual-electrode DC electric-smelting furnace for magnesium.

Figure 1:
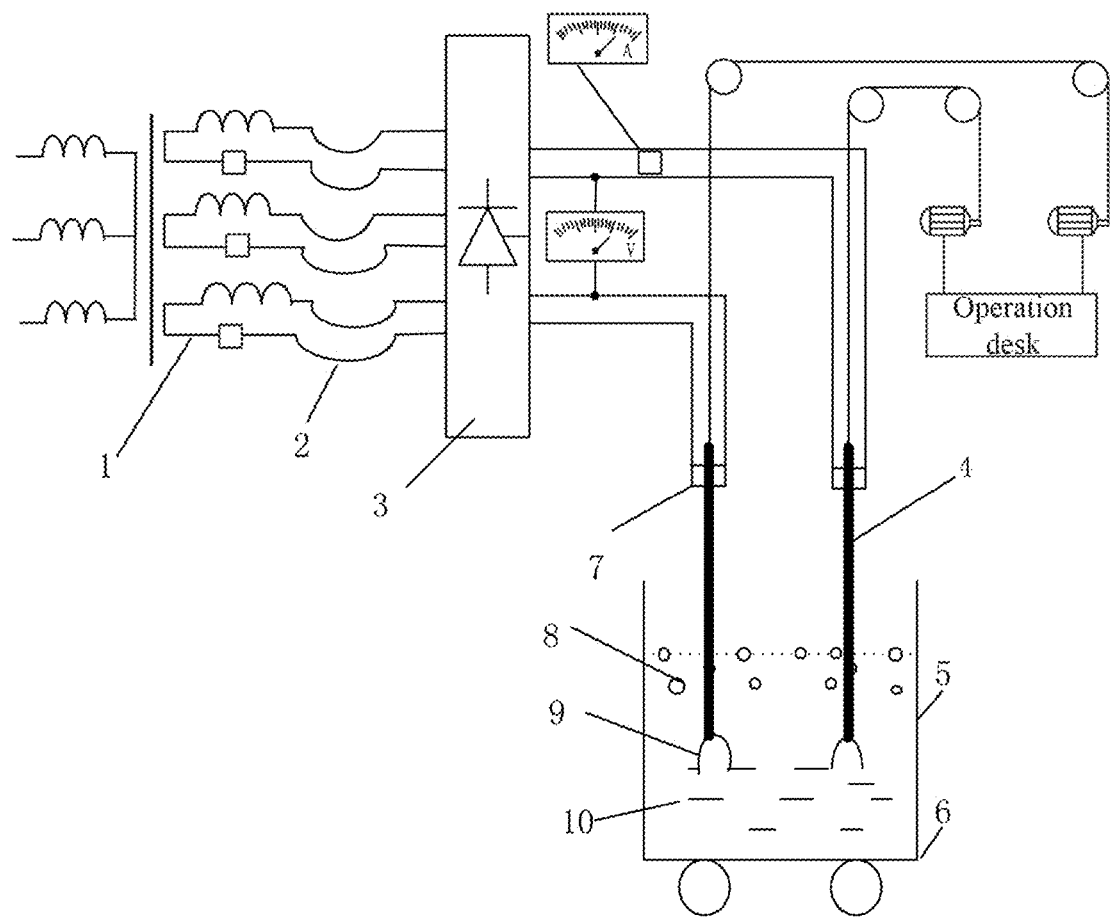
FIG. 1 shows a structural diagram of the electric-smelting furnace for magnesium, wherein 1 indicates transformer, 2 indicates short net, 3 indicates thyristor circuit, 4 indicates graphite electrode, 5 indicates furnace shell, 6 indicates cart body, 7 indicates electrode holder, 8 indicates raw material, 9 indicates electric arc, and 10 indicates smelting pool; 11 indicates electrode; 12 indicates electrode; 13 indicates deflected electric arc; 14 indicates electrode.
Figure 2:
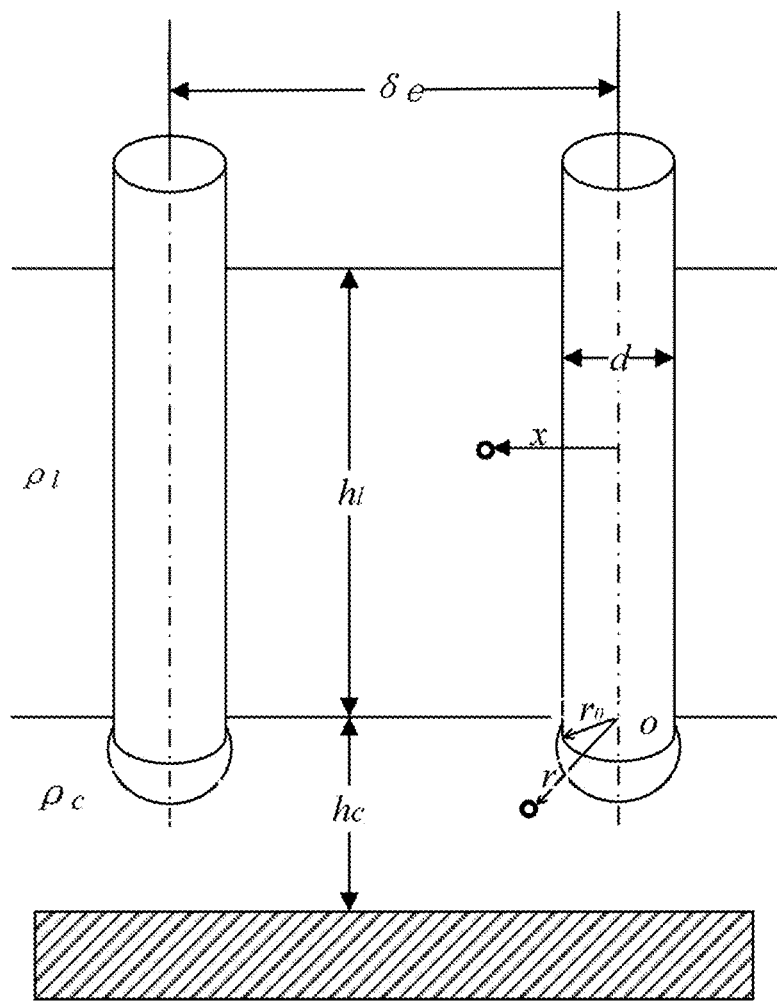
FIG. 2 shows a diagram of the raw material resistance and upper-layer smelting pool resistance of the electric-smelting furnace for magnesium, wherein $\delta_e$ refers to the distance between the center lines of the two electrodes in the dual-electrode DC electric-smelting furnace for magnesium, and d refers to the diameter of the electrode; $h_l$ refers to the inserting depth of the electrode in the raw materials (also called the height of the raw material layer), and $\rho_l$ refers to the resistivity of raw material; $h_c$ refers to the height from the lower end of the electrode to the surface of the smelting pool (also called the height of upper-layer smelted matter), and $\rho_c$ refers to the resistivity of the smelted layer; a bottom shaded area is a smelted layer with good conductivity, which is considered as a smelted product with low resistivity and usually ignored; the end of the electrode is a semi-sphere with a radius of $r_0$.
Figure 3:
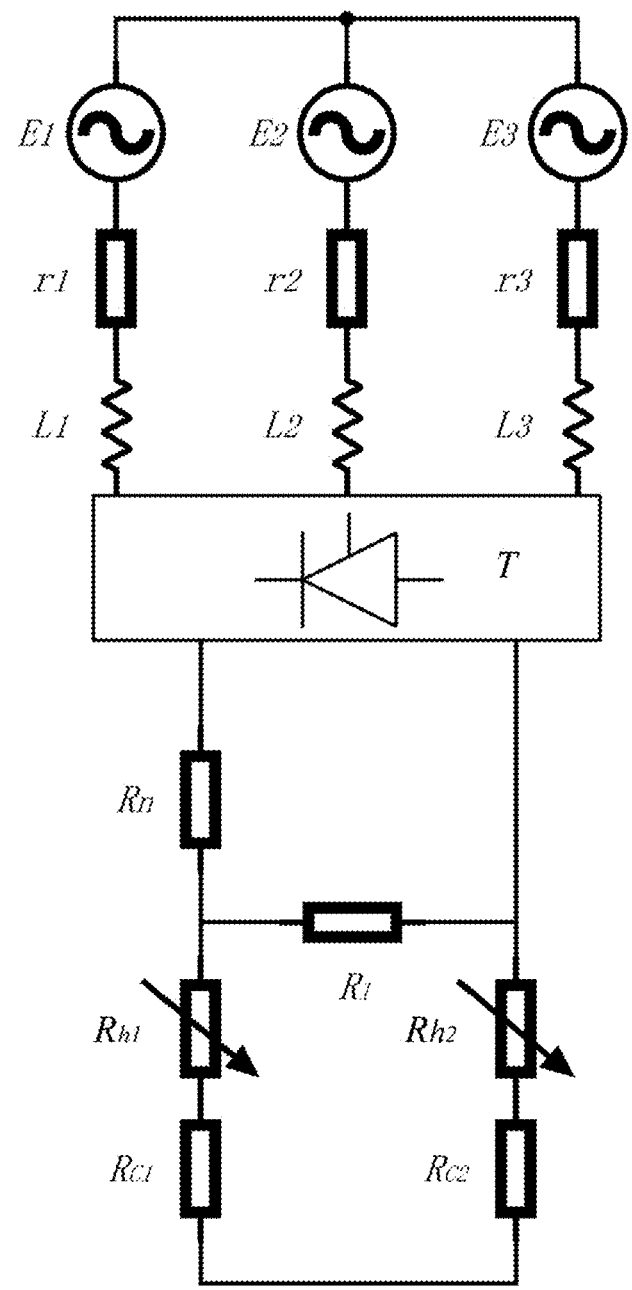
FIG. 3 shows a circuit diagram of the electric-smelting furnace for magnesium, disclosed by the invention, wherein $E_1$-$E_3$ refer to the secondary-side voltages of the transformer, $r_1$-$r_3$ refer to the internal resistance of the transformer, $L_1$-$L_3$ refer to the inductive reactance of the transformer, T refers to the thyristor circuit, $R_n$ refers to equivalent short-net resistance, $R_l$ refers to raw material resistance, $R_{h1}$-$R_{h2}$ refers to arc resistance, and $R_{c1}$-$R_{c2}$ refers to smelting pool resistance.
Figure 4:
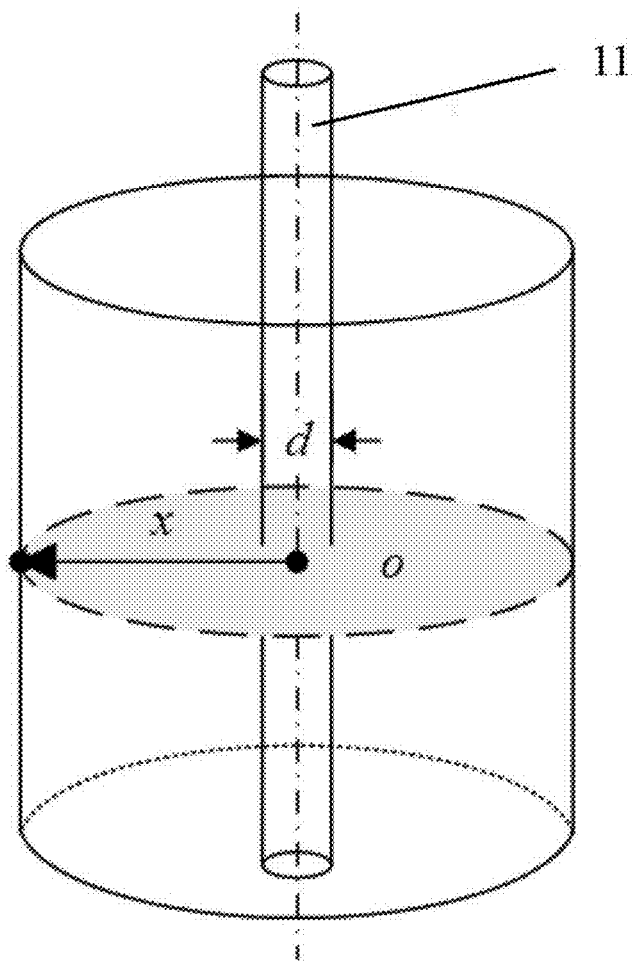
FIG. 4 shows a raw material model of the embodiment of the invention.

The raw material resistance is the resistance of an un-smelted furnace material area. The current radiating and flowing out from the circumferential side of the electrode passes through the resistance to become thermal energy. The value of the raw material resistance is mainly related with the composition of the raw material, the inserting depth of the electrode in the furnace material, the distance between the electrodes, and the temperature of the raw material area. Normally, the raw material resistance is greater than smelting pool resistance. Therefore, only a small part of the electrode current flows through the raw material resistance. The electrode 11-centered cylindrical model as shown in FIG. 4 is established, with the electrode diameter of d (cm).

Step 1.2: determining the electric-field strength of each point in the electric field generated by the raw material layer around the electrode in the cylindrical model by using the micro form of Ohm's law; setting $R_l$ as the raw material resistance between the two electrodes, and $R_c$ as the resistance of the reaction zone at the lower end of the electrode namely smelting pool resistance; when the electric-smelting furnace for magnesium operates, an electric field is formed in the material layer around the electrode.

According to Ohm's law, the formula of the electric-field strength (V/cm) of a certain point in the electric field is:

$$E = \rho J = \rho \frac{I_0}{S_0} \tag{1}$$

wherein $\rho$ refers to the resistivity ($\Omega \cdot$cm) of the electric-field medium, J refers to the current density (A/cm$^2$) of the point, $I_0$ refers to the current at the point, and $S_0$ refers to the cross-sectional area at the point.

Therefore, the electric-field strength $E_l$ at a point being x away from the center line of the electrode in the cylindrical model is as follows:

$$E_l = \rho_l J_l = \rho_l \frac{I_l}{2\pi x h_l} \tag{2}$$

wherein $\rho_l$ refers to the resistivity of raw material, namely the resistivity ($\Omega \cdot$cm) of the raw material layer (with a depth of $h_l$) between the two electrodes; $J_l$ refers to the current density flowing through raw material; $h_l$ refers to the depth (cm) of the electrode in raw material; and $I_l$ refers to the current (A) passing through the raw material layer between the two electrodes.

Step 1.3: integrating the electric-field strength being x away from the center line of the electrode in the cylindrical model from the surface of the electrode to half the distance between the center lines of the two electrodes to obtain half the raw material voltage between the two electrodes, and calculating the raw material voltage between the two electrodes.

The micro voltage difference $dU_x$ of raw material being x away from the center line of the electrode is as follows:

$$dU_x = -E_l dx = -\frac{\rho_l I_l}{2\pi x h_l} \times \frac{dx}{x} \tag{3}$$

The electric-field strength $E_l$ being x away from the center line of the electrode in the cylindrical model is integrated from the surface of the electrode to half $\delta_e/2$ of the distance between the center lines of the two electrodes to obtain half $U_n/2$ of the raw material voltage between the two electrodes:

$$U_n/2 = \int_{U_0}^{U_l} dU_x = -\frac{\rho_l I_l}{2\pi x h_l} \int_{\frac{d}{2}}^{\frac{\delta_e}{2}} \frac{dx}{x} \tag{4}$$

wherein $U_l$ refers to the voltage of the raw material between the two electrodes relative to the center of the electrode, and $U_0$ refers to the voltage of the electrode surface relative to the center of the electrode. The raw material voltage $U_n$ between the two electrodes is as follows:

$$U_n = 2(U_0 - U_l) = -\frac{\rho_l I_l}{\pi h_l} \ln \frac{\delta_e}{d}. \tag{5}$$

Step 1.4: calculating the raw material resistance $R_l$ between the two electrodes:

$$R_l = \frac{U_n}{I_l} = \frac{\rho_l}{\pi h_l} \ln \frac{\delta_e}{d} \tag{6}$$

$\delta_e/d$ for the electric-smelting furnace for magnesium is within the range of 2.2-2.3 in most cases. If the value is too small, electro-thermal conversion is insufficient and electrode configuration is difficult; if the value is too large, change in the effect on electro-thermal conversion is very little, without practical significance.

Step 2: calculating the electric arc-resistance relation model: determining the relation between the actual electric arc length and the distance from the electrode to the surface of the smelting pool, and calculating the relation between the electric arc voltage and the actual electric arc length, namely the electric arc-resistance relation model.

Step 2.1: determining the electric arc-resistance relation model:

$$U_h = U_x + bL_a \tag{7}$$

wherein $U_n$ refers to the arc voltage (V), $U_x$ refers to electric arc quenching voltage (V), b refers to arc voltage coefficient (V/cm), and $L_a$ refers to the arc length (cm).

Step 2.2: according to a model of electric arc voltage and volt-ampere characteristics provided by Bowman, as well as the electrical behavior of the DC electric arc in steady state, describing the electric arc voltage by using the ideal electric arc length and the current change:

$$U_h = \frac{I\rho_a}{k\pi} \cdot \left[ -\frac{1}{m^2 + mn} + \frac{1}{m^2 + mn \cdot \exp(kL)} + \frac{\ln(m+n)}{m^2} + \frac{kL}{m^2} - \frac{\ln[m + n \cdot \exp(kL)]}{m^2} \right] \tag{8}$$

$$m = 3.2 r_k$$

$$n = -2.2 r_k$$

$$k = -\frac{1}{5 r_k}$$

$$r_k = \sqrt{\frac{I}{\pi j_a}}$$

wherein $\rho_a$ refers to the resistivity ($\Omega \cdot$cm) of the electric arc, $j_a$ refers to the current density (kA·cm$^{-2}$) at the negative-pole point, I refers to the arc current (A), $r_k$ refers to the radius (cm) of the negative-pole attachment point, $U_h$ refers to the arc voltage (V), and L refers to the ideal arc length (cm).

Step 2.3: establishing the electric arc magnetic-field model and the electric arc deflection trajectory model by assumptions on the shape and position of electric arcs during operation of the electric-smelting furnace for magnesium.

Step 2.3.1: making theoretical model assumptions on actual electric arcs, and establishing the electric arc magnetic-field model, namely the sum of the electrode-generated magnetic field and the electric arc-generated magnetic field.

Firstly, electric arcs are assumed to have mutual deflections only, namely the main electric arc deflection effect occurs in the plane defined by the two electrodes.

Secondly, the electrode length is assumed to be infinite, namely the ultimate effect (this is a reasonable assumption, because the length of the electrode is far greater than the length of electric arcs affected by the electrode in typical design of the electric-smelting furnace for magnesium) is ignored.

Third, electric arcs are assumed to follow a straight line in deflection.

At last, a magnetic field generated by the majority of the current passing through the smelting pool cannot affect the above electric arcs greatly.

Figure 6:
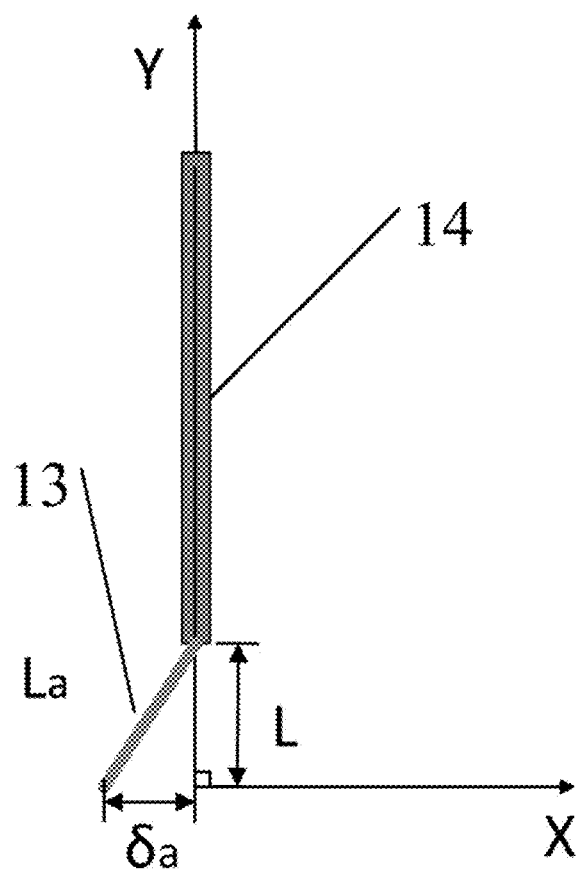
FIG. 6 shows an electric arc deflection trajectory model of the embodiment of the invention, wherein $L_a$ refers to the actual electric arc length, and $\delta_a$ refers to the distance from the center line of the electrode to the electric arc connecting position on the electroplated surface and is used as a measure of electric arc deflection.

As shown in FIG. 6, $L_a$ refers to the actual electric arc length, namely the distance from the projective point of the electric arc on the surface of the smelting pool to the electrode tip; $\delta_a$ refers to the distance from the projective point of the electric arc on the surface of the smelting pool to the center line of the electrode, namely a measure of electric arc deflection.

According to the electromagnetic theory, the following formula is true:

$$dB = \frac{\mu_0}{4\pi} \frac{IdI \times r}{|r|^2} \quad (9)$$

wherein B refers to a magnetic-field vector; $\mu_0$ refers to magnetic permeability (constant) of free space; I refers to the current carried by the current-carrying element; dI refers to the differential distance vector of the current-carrying element, r refers to the distance vector from dI to point $A(x_0, y_0)$ in space B, and $A(x_0, y_0)$ refers to a randomly selected point.

The magnetic-field vector B only consists of the Z component perpendicular to the X-Y plane, namely $B=(0, 0, B_z)$, wherein $B_z$ is a scalar and the Z component is perpendicular to the X-Y plane.

The expression of $B_z$ is obtained by adding the integration of formula (9) over the electrode length and the integration of formula (9) over the ideal electric arc length:

$$B_{z,e} = \frac{\mu_0 I}{4\pi x_0}\left(1 + \frac{y_0 - L}{\sqrt{x_0^2 + (y_0 - L)^2}}\right) \quad (10)$$

$$B_{z,a} = \frac{\mu_0 I}{4\pi\left(\frac{\delta_a}{L}y_0 + x_0\right)} \left( \frac{\frac{\delta_a}{L}x_0 - y_0 + L + \frac{\delta_a^2}{L}}{\sqrt{\left(x_0 + \frac{\delta_a^2}{L}\right)^2 + (y_0 - L)^2}} - \frac{\frac{\delta_a}{L}x_0 - y_0}{\sqrt{x^2 + y^2}} \right)$$

wherein $(x_0, y_0)$ refers to the coordinates of point A to be calculated in the electric arc deflection plane; and $B_{z,e}$ and $B_{z,a}$ respectively refer to the electrode-generated magnetic field and the electric arc-generated magnetic field.

The sum of the electrode-generated magnetic field and the electric arc-generated magnetic field is taken as the established electric arc magnetic-field model: $B_z=B_{z,e}+B_{z,a}$.

Step 2.3.2: determining the motion trajectory of electric arcs in the X-Y plane (namely the electric arc deflection trajectory follows a circular path), and establishing the electric arc deflection trajectory model.

In order to calculate the shape of the arc column, the differential motion equation of free particles of current-carrying electric arc plasma gas needs to be calculated. The particles are a part of high-speed gas jet emitted near the electric arc attachment area on the surface of the electrode, and can be affected by the magnetic field when moving between the electrode and the smelting pool.

According to basic electromagnetic mechanics, the following equation is true:

$$dF = IdI \times B \quad (11)$$

wherein dF refers to the force applied on the current-carrying element N with a length of |dI| in the electric arc at current strength I and magnetic-field strength B. I is defined in the direction of the current flow vector, and the coordinates of the current-carrying element N in the magnetic field are $(x_0, y_0)$ at some points.

The following are obtained by considering the motion in the X-Y plane:

$$dI = \hat{i}|dI| = \quad (12)$$

$$\left(\frac{dx}{\sqrt{dx^2 + dy^2}}, \frac{dy}{\sqrt{dx^2 + dy^2}}, 0\right)|dI| = (dx, dy, 0)\frac{|dI|}{\sqrt{dx^2 + dy^2}}$$

$$dI\frac{dt}{dt} = \left(\frac{dx}{dt}, \frac{dy}{dt}, 0\right)\frac{|dI|}{\sqrt{\left(\frac{dx}{dt}\right)^2 + \left(\frac{dy}{dt}\right)^2}} = (v_x, v_y, 0)\frac{|dI|}{\sqrt{v_x^2 + v_y^2}}$$

$$B = (0, 0, B_z)$$

$$dF = dma = \pi r_a^2 \rho_a |dI|\left(\frac{dv_x}{dt}, \frac{dv_y}{dt}, 0\right)$$

wherein $v_x$ and $v_y$ refer to the velocity component of the current-carrying element N selected in the electric arc respectively in X direction and Y direction, dm refers to the differential mass of the current-carrying element N, a refers to the acceleration vector of the current-carrying element N, $r_a$ refers to the radius of the current-carrying element N, and $\rho_a$ refers to arc plasma density.

Based on the definitions of dI, B and dF, the above formula can be converted to:

$$\frac{\pi r_a^2 \rho_a}{I}\left(\frac{dv_x}{dt}, \frac{dv_y}{dt}, 0\right) = \frac{1}{\sqrt{v_x^2 + v_y^2}}(v_y B_z, -v_x B_z, 0) \quad (13)$$

The following assumptions lie in that: $B_z$ approximates to a constant, and the velocity vector is constant in magnitude and equals to the velocity $v_a$ of electric arc plasma.

The following are obtained by transforming formula (13):

$$\frac{\pi r_a^2 \rho_a v_a}{IB_z}\left(\frac{dv_x}{dt}, \frac{dv_y}{dt}, 0\right) = (v_y, -v_x, 0) \quad (14)$$

$$\dot{v}_y = \alpha v_y$$

$$\dot{v}_y = -\alpha v_x$$

$$\alpha = \frac{IB_z}{\pi r_a^2 \rho_a v_a}$$

The simultaneous differential equations in formula (14) have the standard forms of harmonic motion:

$$v_x = A \sin(\alpha t) + B \cos(\alpha t)$$

$$v_y = -B \sin(\alpha t) + A \cos(\alpha t) \quad (15)$$

wherein both A and B are integration constants;

$$\sqrt{v_x^2+v_y^2}=\sqrt{(A^2+B^2)\sin^2(\alpha t)+(A^2+B^2)\cos^2(\alpha t)}=\sqrt{A^2+B^2} \quad (16)$$

As both A and B are constants, $v_a$ are indeed constant during the entire motion and the assumption is reasonable.

Again, formula (15) is integrated into the positions x and y of the current-carrying element N as the functions of time:

$$x = C - \frac{A}{\alpha}\cos(\alpha t) + \frac{B}{\alpha}\sin(\alpha t) \quad (17)$$

$$y = D + \frac{B}{\alpha}\cos(\alpha t) + \frac{A}{\alpha}\sin(\alpha t)$$

wherein C and D are integration constants.

Then the electric arc deflection trajectory model is obtained:

$$(x-C)^2 + (y-D)^2 = \frac{A^2+B^2}{\alpha^2} \quad (18)$$

The above is an equation of a circle in the X-Y plane. Therefore, the electric arc deflection trajectory follows a circular path when moving between the electrode and the smelting pool; an obvious curve can be formed when the electric arc from the electric arc ejector moves between the electrode and the bath liquid.

Step 2.4: determining the relation between the actual electric arc length $L_a$ and the ideal electric arc length L in combination with the radius $R_a$ of the electric arc deflection trajectory as well as the electric arc deflection trajectory model.

Once the electric arc deflection trajectory model is obtained, the actual electric arc length is not the distance from the tail end of the electrode to the surface of the smelting pool, and the effect of electric arc deflection on the electric arc voltage can also be changed.

The actual electric arc length $L_a$ is:

$$L_a = \oint dl = \int_0^{L_a}\left(\sqrt{\left(\frac{dx}{dy}\right)^2+1}\right)dy \quad (19)$$

In the case of the initial electric arc trajectory facing down vertically from the electrode: $R_a^2=(A^2+B^2)/\alpha^2$, the following is obtained from formula (18):

$$(x-R_a)^2+(y-L)^2=R_a^2 \quad (20)$$

In combination with formula (19), the relation between the actual electric arc length $L_a$ and the ideal electric arc length L is obtained:

$$L_a = R_a \arcsin\left(\frac{L}{R_a}\right) \quad (21)$$

Figure 7:
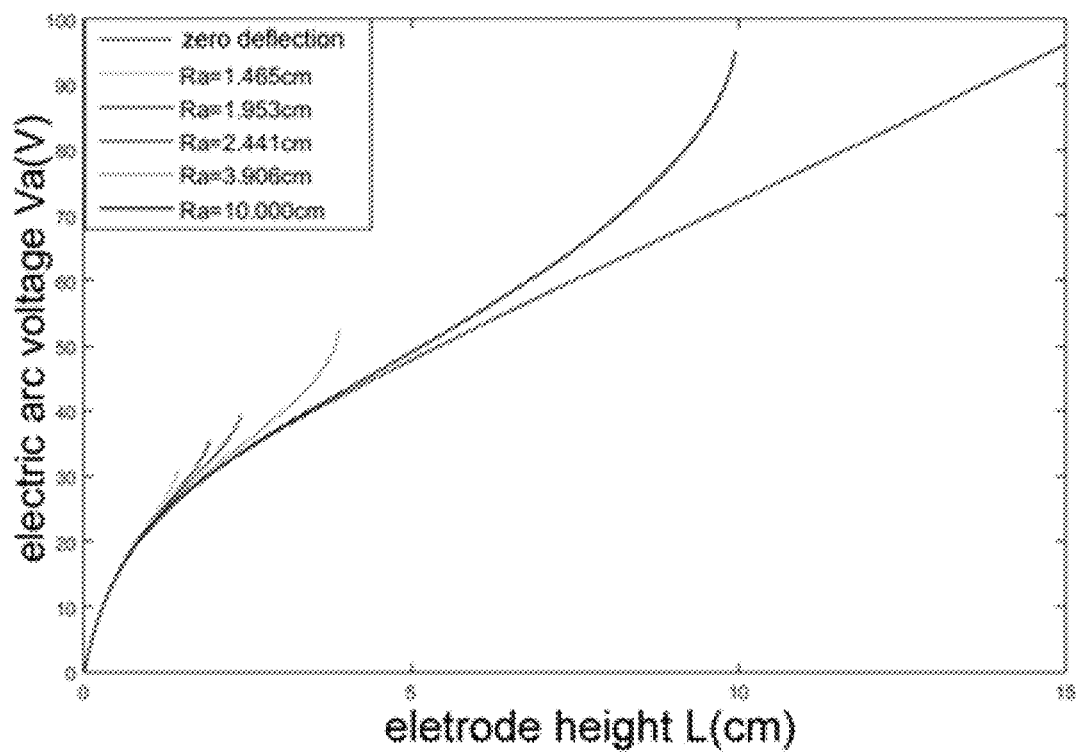
FIG. 7 shows curves for the relation between the theoretical voltage and the electrode height.

Curves for the relation between the theoretical voltage and the electrode height of the dual-electrode furnace for magnesium can be produced by replacing L in formula (8) with $L_a$. FIG. 7 shows several curves for the relation between the theoretical voltage and the electrode height with different radii $R_a$ of electric arc deflection trajectories.

Step 2.5: calculating the relation between the electric arc voltage and the actual electric arc length $L_a$, namely the model of the electric arc-resistance relation.

While the electrode moves, the electric arc voltage curve is still close to that of an un-deflected electric arc if the electrode height is quite small compared with the radius $R_a$ of the electric arc deflection trajectory. As the electrode height approaches the radius $R_a$ of the electric arc deflection trajectory, the curves separate. The electric arc showing obvious electric arc deflection in the dual-electrode furnace can have a voltage 30% higher than the un-deflected electric arc in the Bowman model.

Step 3: calculating smelting pool resistance, namely the sum in series of the smelting pool resistance of the two electrodes.

Figure 5:
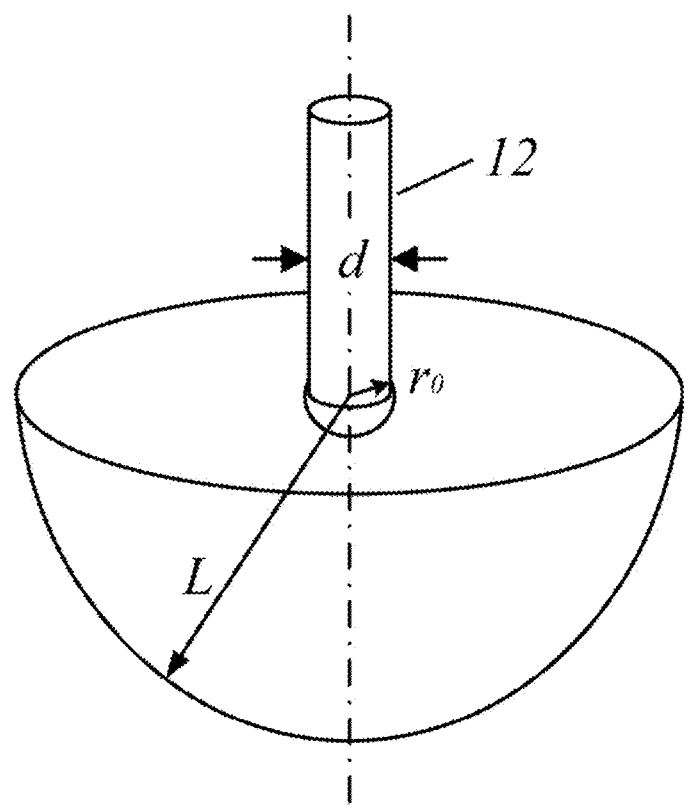
FIG. 5 shows a smelting pool model of the embodiment of the invention.

Step 3.1: establishing a simplified smelting pool model: simplifying the smelting pool model as a semi-sphere model with the bottom center of the electrode as the center of sphere and the distance from the bottom of the electrode to the surface of the smelting pool as the radius, wherein smelting pool resistance is the resistance of the reaction zone below the electrode; the current flowing from the lower surface of the electrode passes through smelting pool resistance to become thermal energy; the value of smelting pool resistance mainly depends on the distance from the lower end of the electrode to the bottom of the electric-smelting furnace for magnesium, and the size and the temperature of the reaction zone below the electrode. Normally, smelting pool resistance is very little, and most of the current of the electrode flows through smelting pool resistance, and the semi-sphere model is as shown in FIG. 5.

Step 3.2: determining the electric-field strength $E_c$ of the spherical surface being r away from the center of sphere in the semi-sphere model by using the micro form of Ohm's law.

In the semi-sphere model with the bottom center of the electrode as the center of sphere, the electric-field strength $E_c$ of the spherical surface being r away from the center of sphere is:

$$E_c = \rho_c \frac{I_c}{S} = \frac{\rho_c I_c}{2\pi r^2} \quad (22)$$

The micro potential differential $dU_r$ of the spherical surface being r away from the center of sphere can be derived from the micro form of Ohm's law:

$$dU_r = -E_c dr = -\rho_c \frac{I_c}{S}dr = -\frac{\rho_c I_c}{2\pi r^2}dr. \quad (23)$$

Step 3.3: integrating the electric-field strength being r away from the center of sphere in the semi-sphere model from the bottom of the electrode to the surface of the smelting pool so as to obtain voltage drop from the bottom of the single electrode to the surface of the smelting pool; integrating the electric-field strength $E_c$ being r away from the center of sphere from the bottom of the electrode to the surface of the smelting pool to obtain $U_c$, namely voltage drop from the bottom of the single electrode to two ends of smelting pool resistance, setting the voltage drop from the bottom center of the electrode to the surface of the smelting pool as $U_l$, the voltage drop from the bottom center of the electrode to the bottom of the electrode as $U_0$, and setting $r_0$ as the radius of the electrode; the following is obtained:

$$U_c = \int_{U_0}^{U_1} dU_r = -\frac{\rho_c I_c}{2\pi} \int_{r_0}^{h_c} \frac{dr}{r^2} \quad (24)$$

The voltage drop from the bottom of the single electrode to the surface of the smelting pool is:

$$U_c = U_1 - U_0 = \frac{\rho_c I_c}{2\pi}\left(\frac{1}{r_0} - \frac{1}{h_c}\right) \quad (25)$$

Step 3.4: calculating the sum in series of the smelting pool resistance of the two electrodes, namely the determined smelting pool resistance $R_c$.

The sum in series of the smelting pool resistance of the two electrodes is the smelting pool resistance $R_c$:

$$R_c = 2 \times \frac{U_c}{I_c} = \frac{\rho_c}{\pi r_0}\left(1 - \frac{r_0}{h_c}\right) \quad (26)$$

As can be known from the formula, when the electrodes are infinitely close to the surface of the smelting pool (namely $h_c \rightarrow r_0$), smelting pool resistance is $0\Omega$; as the electrodes move far away from the surface of the smelting pool, an abstract conception with playing a guiding role can be derived: when $h_c \gg r_0$, $$R_c = \frac{\rho_c}{\pi r_0} \quad (27)$$

The smelting pool resistance at this time tends to be a constant value (industrial value).

While the embodiment of the present invention has been described above, those skilled in the art should understand that the embodiment is only provided by examples. The embodiment can have numerous changes or variations without departing from the principle and essence of the invention. The scope of the invention is limited only by the appended claims.

What is claimed is:

1. A calculation method for operating resistance in a dual-electrode DC electric-smelting furnace for magnesium, comprising the following steps of:
    calculating a raw material resistance: simplifying a raw material model as an electrode-centered cylindrical model, determining an electric-field strength of each point in an electric field generated by a raw material layer around an electrode in the cylindrical model, calculating a raw material voltage between two electrodes according to the electric-field strength of each point in the electric field, and further obtaining the raw material resistance between the two electrodes;
    calculating an electric arc-resistance relation model: determining a relation between an actual electric arc length and a distance from the electrode to a surface of a smelting pool, and calculating a relation between an electric arc voltage and the actual electric arc length, namely the electric arc-resistance relation model;
    calculating a smelting pool resistance, namely a sum in series of the smelting pool resistance of the two electrodes; and
    controlling an output power of the dual-electrode DC electric-smelting furnace for magnesium based on the raw material resistance and the smelting pool resistance,
    wherein the calculating the smelting pool resistance comprises:
        simplifying a smelting pool model as a semi-sphere model with a bottom center of the electrode as a center of a sphere and a distance from a bottom of the electrode to a surface of the smelting pool as a radius;
        calculating an electric-field strength of a spherical surface being a distance r away from the center of the sphere in the semi-sphere model;
        integrating the electric-field strength being the distance r away from the center of sphere in the semi-sphere model from the bottom of the electrode to the surface of the smelting pool so as to obtain a voltage drop from the bottom of the single electrode to the surface of the smelting pool; and
        calculating the sum in series of the smelting pool resistance of the two electrodes, namely the calculated smelting pool resistance.

2. The method according to claim 1, wherein the calculating the raw material resistance comprises:
    simplifying the raw material model as the electrode-centered cylindrical model according to an inserting depth of the electrode in a raw material and a distance between center lines of the two electrodes in the dual-electrode DC electric-smelting furnace for magnesium;
    determining the electric-field strength of each point in the electric field generated by the raw material layer around the electrode in the cylindrical model; and
    integrating the electric-field strength being a distance x away from the center line of the electrode in the cylindrical model from a surface of the electrode to half the distance between the center lines of the two electrodes to obtain half the raw material voltage between the two electrodes, and calculating the raw material voltage between the two electrodes so as to further obtain the raw material resistance.

3. The method according to claim 1, wherein the calculating electric-arc resistance relation model comprises:
    determining the electric arc-resistance relation model;
    describing the electric arc voltage according to changes of an ideal electric arc length and a current;
    establishing an electric arc magnetic-field model and an electric arc deflection trajectory model by assumptions on shape and position of electric arcs during an operation of the electric-smelting furnace for magnesium;
    determining a relation between the actual electric arc length and the ideal electric arc length in combination with a radius of an electric arc deflection trajectory as well as the electric arc deflection trajectory model; and
    calculating a relation between the electric arc voltage and the actual electric arc length, namely the electric arc-resistance relation model.

4. The method according to claim 3, wherein the electric arc deflection trajectory model is as follows:

$$L_a = R_a \arcsin\left(\frac{L}{R_a}\right)$$

wherein $R_a$ is an electric arc deflection trajectory radius, $L_a$ is the actual electric arc length and L is the ideal electric arc length namely the distance from the electrode to a surface of the smelting pool.

5. The method according to claim 3, wherein the establishing the electric arc magnetic-field model and the electric arc deflection trajectory model by assumptions on the shape and position of the electric arcs during the operation of the electric-smelting furnace for magnesium comprises:

making theoretical model assumptions on actual electric arcs, and establishing the electric arc magnetic-field model, namely a sum of an electrode-generated magnetic field and an electric arc-generated magnetic field; and determining a motion trajectory of the electric arcs in an X-Y plane, namely, the electric arc deflection trajectory following a circular path, and establishing the electric arc deflection trajectory model.

6. The method according to claim 5, wherein the making theoretical model assumptions on the actual electric arcs comprises that:

the electric arcs are assumed to have mutual deflections only, namely a main electric arc deflection effect occurs in a plane defined by the two electrodes;

an electrode length is assumed to be infinite, wherein an ultimate effect is ignored;

the electric arcs are assumed to follow a straight line in deflection; and an effect of a magnetic field generated by a current of the smelting pool on the electric arc is ignored.

\* \* \* \* \*